(12) United States Patent
Parker

(10) Patent No.: US 11,931,224 B1
(45) Date of Patent: Mar. 19, 2024

(54) TOOTH POD

(71) Applicant: Robert Parker, Coos Bay, OR (US)

(72) Inventor: Robert Parker, Coos Bay, OR (US)

( * ) Notice: Subject to any disclaimer, the term of this patent is extended or adjusted under 35 U.S.C. 154(b) by 0 days.

(21) Appl. No.: 18/210,519

(22) Filed: Jun. 15, 2023

Related U.S. Application Data

(60) Provisional application No. 63/433,699, filed on Dec. 19, 2022.

(51) Int. Cl.
*A61C 8/00* (2006.01)
*A61C 8/02* (2006.01)
*A61C 19/06* (2006.01)
*A61F 2/28* (2006.01)

(52) U.S. Cl.
CPC .......... *A61C 8/0004* (2013.01); *A61C 19/063* (2013.01); *A61F 2002/2817* (2013.01)

(58) Field of Classification Search
CPC ................ A61C 8/0004; A61C 19/063; A61F 2002/2817
USPC ........................................................ 433/215
See application file for complete search history.

(56) References Cited

U.S. PATENT DOCUMENTS

| | | | |
|---|---|---|---|
| 3,069,773 A | 12/1962 | Saffir | |
| 3,413,723 A | 12/1968 | Degussa | |
| 3,845,770 A * | 11/1974 | Theeuwes | A61F 6/144 424/432 |
| 3,916,899 A * | 11/1975 | Theeuwes | A61K 9/0004 424/435 |
| 4,321,042 A | 3/1982 | Scheicher | |
| 4,327,725 A * | 5/1982 | Cortese | A61K 9/0004 424/431 |
| 5,200,195 A * | 4/1993 | Dong | A61K 9/0004 424/464 |
| 5,372,503 A | 12/1994 | Elia | |

(Continued)

FOREIGN PATENT DOCUMENTS

| | | |
|---|---|---|
| CA | 1113970 A | 12/1981 |
| CA | 1117255 A | 2/1982 |

(Continued)

OTHER PUBLICATIONS

David T. Wu, Polymeric Scaffolds for Dental, Oral, and Craniofacial Regenerative Medicine, Molecules 2021, 26, 7043. https://doi.org/10.3390/molecules26227043.

(Continued)

*Primary Examiner* — Matthew M Nelson
(74) *Attorney, Agent, or Firm* — Jafari Law Group, Inc.

(57) ABSTRACT

The present invention discloses a method and a device or tooth pod for regeneration of teeth. In some exemplary embodiments, a method of implanting a tooth pod comprises of providing a tooth pod, implanting the tooth pod into an insertion point, and sealing the insertion point. The tooth pod comprises a composition of vitamin E oil and penicillin. In some exemplary embodiments, the tooth pod comprises of a permeable membrane defined by an outer layer and an inner layer, and a cavity defined by the space enclosed within the inner layer. In some exemplary embodiments, the device is a spherical pod. The tooth pod is implanted into the gum line at approximately ½ the depth of a tooth, which provides space to growth of tooth upwards and downwards. The blood fills the hollow space of the tooth pod and forms nerve roots. Thereafter, a new adult tooth is formed.

10 Claims, 3 Drawing Sheets

(56) References Cited

U.S. PATENT DOCUMENTS

| | | | |
|---|---|---|---|
| 5,573,401 A | 11/1996 | Davidson et al. | |
| 5,869,096 A * | 2/1999 | Barclay | A61K 9/0004 424/435 |
| 7,708,557 B2 | 5/2010 | Rubbert | |
| 8,231,387 B2 | 7/2012 | Salvi | |
| 8,628,325 B2 | 1/2014 | Vachtenberg | |
| 8,684,734 B1 | 4/2014 | Lyren | |
| 9,566,135 B2 | 2/2017 | Elia | |
| 9,707,321 B2 | 7/2017 | Daigo | |
| 9,763,752 B2 | 9/2017 | Dosta et al. | |
| 10,098,845 B2 * | 10/2018 | Hsu | A61K 9/4808 |
| 11,759,417 B2 * | 9/2023 | Dong | A61K 31/522 424/473 |
| 2006/0127437 A1 | 6/2006 | Kennedy | |
| 2009/0148486 A1 | 6/2009 | Lu | |
| 2010/0015200 A1 | 1/2010 | McClain et al. | |
| 2010/0015576 A1 | 1/2010 | Altshuler et al. | |
| 2011/0280924 A1 | 11/2011 | Lin | |
| 2014/0200678 A1 | 7/2014 | Detamore | |
| 2016/0243036 A1 * | 8/2016 | Paiement | A61K 31/704 |
| 2017/0156824 A1 | 6/2017 | Rubbert et al. | |
| 2019/0001025 A1 | 1/2019 | Ferrari et al. | |
| 2020/0275998 A1 | 9/2020 | Lomicka | |

FOREIGN PATENT DOCUMENTS

| | | |
|---|---|---|
| CN | 1997421 A | 7/2007 |
| CN | 105662621 A | 6/2016 |
| CN | 103892930 B | 4/2017 |
| CN | 106901852 A | 6/2017 |
| CN | 107536651 A | 1/2018 |
| CN | 107997838 A | 5/2018 |
| CN | 108114322 A | 6/2018 |
| CN | 108553187 A | 9/2018 |
| CN | 105662621 B | 10/2018 |
| CN | 208823014 A | 5/2019 |
| CN | 208958366 U | 6/2019 |
| CN | 106178124 B | 10/2019 |
| CN | 110403721 B | 8/2021 |
| DE | 19957857 A1 | 11/2000 |
| ES | 2284236 T3 | 11/2007 |
| JP | 04141163 A | 5/1992 |
| JP | 4061581 B2 | 3/2008 |
| KR | 100279178 B1 | 1/2001 |
| KR | 20150114710 A | 10/2015 |
| KR | 20210044168 A | 4/2021 |
| RU | 2023437 C1 | 11/1994 |
| WO | 1998047439 A2 | 10/1998 |
| WO | 2003082188 A2 | 10/2003 |
| WO | 2005046746 A2 | 5/2005 |
| WO | 2006090777 A1 | 8/2006 |
| WO | 2015167050 A1 | 11/2015 |
| WO | 2019104852 A1 | 6/2019 |
| WO | 2019223753 A1 | 11/2019 |
| WO | 2019240478 A1 | 12/2019 |

OTHER PUBLICATIONS

Dental Porcelain, Comprehensive Biomaterials II, 2017.

* cited by examiner

TOOTH POD

PRIORITY CLAIM

This is a Non-provisional Application that claims priority to U.S. Provisional Application No. 63/433,699, filed on Dec. 19, 2022, the entire disclosure of which is incorporated by reference in its entirety.

TECHNICAL FIELD OF THE INVENTION

The present disclosure relates generally to dentistry, and more particularly, to a method and a tooth pod or device for regeneration of teeth.

BACKGROUND OF THE INVENTION

Teeth loss is a phenomenon that may occur for any number of reasons during one's life (whether human, mammal, or any other vertebrate). Humans, like most mammals, are diphyodont. In humans, a set of twenty deciduous teeth are replaced by a completely new set of thirty-two permanent adult teeth. If any of these secondary teeth are lost, they will not grow back. Dental implant devices are one of the successful treatment methods for the replacement of missing teeth. Generally, the dental implant device includes a dental implant and a prosthetic device such as an artificial tooth. The dental implant is surgically implanted into a patient's jawbone. The dental implant is adapted to directly or indirectly anchor and support the prosthetic devices. Alternatively, the dental implant is adapted to anchor a dental abutment, which connects the prosthetic device to the dental implant.

One problem with existing dental implants are the unattractive colors of the device. Traditionally, metals like commercially pure titanium and titanium alloys are used for making dental implants and implant components such as abutments, etc. due to their excellent material stability and their good biological integration. However, the implant or abutment that is visible near the gingival margin provides a non-aesthetically pleasing appearance in a person's mouth.

Another problem with existing dental implants that are aesthetically pleasing typically provide inadequate strength resulting in relatively frequent replacement or repair of the device.

Yet another problem with the existing dental implants is loosening of the implant. The bone at where the implant is fixed often does not bond with the implant, which causes loosening of the implant. The loosening of the implant may also be caused by the poor distribution of forces from the implant to the maxilla or mandible. If the load is concentrated on a particular portion of the maxilla or mandible, this stress concentration may cause the bond between implant and maxilla or mandible to weaken. Stress concentrations are typically caused by improper implant design or positioning, or an implant that is not shaped to distribute the tooth load relatively evenly. Further, the dental implant devices are temporary solution, which may fail and often requires replacement or repair of device.

Therefore, there is a need for a permanent solution that could replace the existing dental implant device. Further, there is need for a method and a device that promotes regeneration of teeth.

BRIEF SUMMARY OF THE INVENTION

The present invention discloses a method and a device for regeneration of teeth. The device or tooth pod comprises of vitamin E oil and penicillin. The tooth pod has a permeable membrane defined by the space between an outer layer and an inner layer. The tooth pod has a cavity that is defined by the space within the inner layer. The tooth pod is implanted into the gum line at approximately ½ the depth of the tooth, which provides space to growth of tooth upwards and downwards. The tooth pod is implanted at one or more sites of the human jaw line, where regeneration of teeth is required.

The present invention discloses a method of regenerating a patient's tooth comprising: providing a tooth pod including an outer layer, an inner layer, a permeable membrane defined within the outer layer and the inner layer, and a cavity defined within the inner layer; implanting the tooth pod into an insertion point situated below a gumline and within a tooth socket of a patient; and sealing the insertion point.

In some exemplary embodiments, the permeable membrane is just composed of vitamin E oil and penicillin, which upon saturation allows blood to fill into an inner hollow space. In some exemplary embodiments, the permeable membrane includes a plurality of microscopic pores.

In some exemplary embodiments, the permeable membrane of the tooth pod is adapted to facilitate blood flow into the cavity.

In some exemplary embodiments, the cavity is adapted to receive and retain blood flow.

In some exemplary embodiments, the cavity is adapted to facilitate the coagulation of the retained blood flow.

In some exemplary embodiments, the insertion point is approximately ½" to ¾" below the gumline of the patient.

In some exemplary embodiments, the tooth pod is adapted to be implanted surgically by making an incision into the patient's gum line and pushing the tooth pod down into the insertion point.

In some exemplary embodiments, the tooth pod is adapted to be implanted without making an incision into the patient's gum line.

In some exemplary embodiments, the tooth pod is adapted to be implanted in the insertion point after a tooth extraction.

In some exemplary embodiments, the insertion point is sealed using stitches or sutures.

The present invention further discloses a device or pod for regenerating a tooth of a patient, comprising: a permeable membrane defined by an inner layer and an outer layer, wherein the permeable membrane is adapted to facilitate blood flow; and a cavity defined within the inner layer, wherein the cavity is adapted to receive and retain blood flow, via saturation of the tooth pod.

In some exemplary embodiments, tooth pod is just a hollow gel capsule which allows saturation by blood and consists of vitamin E and penicillin.

In some exemplary embodiments, the permeable membrane is comprised of vitamin E oil and penicillin.

In some exemplary embodiments, the permeable membrane is comprised of at least 500 mg of penicillin.

In some exemplary embodiments, the permeable membrane is adapted to dissolve within a predetermined time period, approximately 1 to 1 and ½ months.

In some exemplary embodiments, the cavity is adapted to receive and retain blood flow through the permeable membrane, via saturation.

In some exemplary embodiments, the device is a round pod.

In some exemplary embodiments, the outer layer of the round pod has a diameter of approximately 0.177 mm.

In some exemplary embodiments, the outer layer of the round pod has a diameter approximately ⅛th of an inch (3.175 mm).

In some exemplary embodiments, the inner layer of the spherical or round pod has a diameter of approximately 1/16th of an inch (1.588 mm).

BRIEF DESCRIPTION OF THE DRAWINGS

Elements in the figures have not necessarily been drawn to scale in order to enhance their clarity and improve understanding of these various elements and embodiments of the present invention. Furthermore, elements that are known to be common and well understood to those in the industry are not depicted in order to provide a clear view of the various embodiments of the invention.

DETAILED DESCRIPTION OF THE INVENTION

Figure 1:
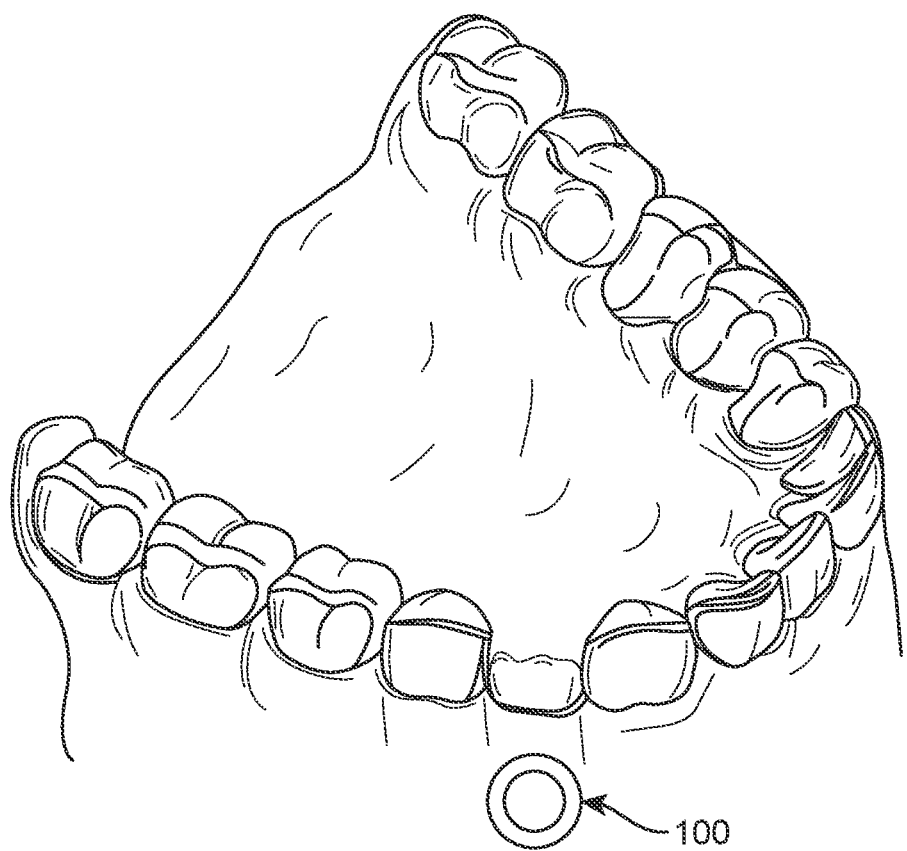
FIG. 1 illustrates a perspective view of a human jaw implanted with a tooth pod for regeneration of teeth in accordance with some exemplary embodiments of the present invention.

In the following discussion that addresses a number of embodiments and applications of the present invention, reference is made to the accompanying drawings that form a part thereof, where depictions are made, by way of illustration, of specific embodiments in which the invention may be practiced. It is to be understood that other embodiments may be utilized, and changes may be made without departing from the scope of the invention. Wherever possible, the same reference numbers are used in the drawings and the following description to refer to the same or similar elements.

In the following detailed description, numerous specific details are set forth by way of examples in order to provide a thorough understanding of the relevant teachings. However, it should be apparent to those skilled in the art that the present teachings may be practiced without such details. In other instances, well known structures, components and/or functional or structural relationship thereof, etc., have been described at a relatively high-level, without detail, in order to avoid unnecessarily obscuring aspects of the present teachings.

Throughout the specification and claims, terms may have nuanced meanings suggested or implied in context beyond an explicitly stated meaning. Likewise, the phrase "in one embodiment/example" as used herein does not necessarily refer to the same embodiment and the phrase "in another embodiment/example" as used herein does not necessarily refer to a different embodiment. It is intended, for example, that claimed subject matter include combinations of example embodiments in whole or in part.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and or steps. Thus, such conditional language is not generally intended to imply that features, elements and or steps are in any way required for one or more embodiments, whether these features, elements and or steps are included or are to be performed in any particular embodiment.

The terms "comprising," "including," "having," and the like are synonymous and are used inclusively, in an open-ended fashion, and do not exclude additional elements, features, acts, operations and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require at least one of X, at least one of Y, and at least one of Z to each be present. The term "and or" means that "and" applies to some embodiments and "or" applies to some embodiments. Thus, A, B, and or C can be replaced with A, B, and C written in one sentence and A, B, or C written in another sentence. A, B, and or C means that some embodiments can include A and B, some embodiments can include A and C, some embodiments can include B and C, some embodiments can only include A, some embodiments can include only B, some embodiments can include only C, and some embodiments include A, B, and C. The term "and or" is used to avoid unnecessary redundancy. Similarly, terms, such as "a, an," or "the," again, may be understood to convey a singular usage or to convey a plural usage, depending at least in part upon context. In addition, the term "based on" may be understood as not necessarily intended to convey an exclusive set of factors and may, instead, allow for existence of additional factors not necessarily expressly described, again, depending at least in part on context.

While exemplary embodiments of the disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Thus, nothing in the foregoing description is intended to imply that any particular feature, characteristic, step, module, or block is necessary or indispensable. Indeed, the novel methods and systems described herein may be embodied in a variety of other forms; furthermore, various omissions, substitutions, and changes in the form of the methods and systems described herein may be made without departing from the spirit of the invention or inventions disclosed herein. Accordingly, the following detailed description does not limit the disclosure. Instead, the proper scope of the disclosure is defined by the appended claims.

As used in this disclosure, the term "comprise" and variations of the term, such as "comprising" and "comprises", are not intended to exclude other additives, components, integers or steps. For purpose of description herein, the terms "upper", "lower", "left", "right", "front", "rear", "horizontal", "vertical" and derivatives thereof shall relate to the invention as oriented in figures. However, it is to be understood that the invention may assume various alternative orientations and step sequences, except where expressly specified to the contrary. It is also to be understood that the specific devices and processes illustrated in the attached drawings, and described in the following specification are simply exemplary embodiments of the inventive concepts defined in the appended claims. Hence, specific dimensions and other physical characteristic relating to the embodiments disclosed herein are not to be considered as limiting, unless the claims expressly state otherwise.

The present invention discloses a method for implanting a tooth pod comprising: providing a tooth pod 100 including an outer layer 102, an inner layer 101, a permeable membrane 103 defined within the outer layer 102 and the inner layer 101, and a cavity 104 defined within the inner layer 101; implanting the tooth pod 100 into an insertion point situated below a gumline and within a tooth socket of a patient; and sealing the insertion point.

Turning now to the figures, FIG. 1 discloses a perspective view of a human jaw implanted with a tooth pod 100 comprising the composition for regeneration of tooth, according to an embodiment of the present invention. More specifically, FIG. 1 illustrates an exemplary implantation of the tooth pod 100 in an insertion point situated below a patient's gum line. In some exemplary embodiments, the insertion point is approximately ½" to ¾" below the gum line of the patient. In some exemplary embodiments, the tooth pod 100 is adapted to be surgically implanted by making an incision into the patient's gum line and pushing the tooth pod 100 down into the insertion point. In some exemplary embodiments, the tooth pod 100 is adapted to be implanted without making an incision into the patient's gum line. For example, the tooth pod 100 can be implanted in the insertion point after a tooth extraction when the insertion point is accessible without incisions.

In some exemplary embodiments, the insertion point is adapted to be sealed. For example, the insertion point can be sealed using temporary stitches.

Figure 2:
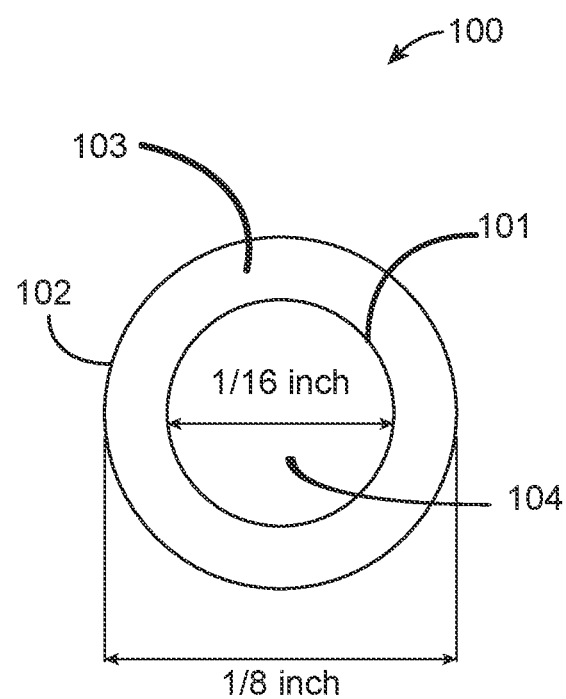
FIG. 2 illustrates a tooth pod for regeneration of teeth in accordance with some exemplary embodiments of the present invention, depicting exemplary dimensions for a permeable membrane of a tooth pod.

Turning now to the next figure, FIG. 2 illustrates the tooth pod 100 for regeneration of teeth in accordance with some exemplary embodiments of the present invention, depicting exemplary dimensions for the permeable membrane 103. In some exemplary embodiments, the permeable membrane 103 of the tooth pod 100 is adapted to facilitate blood flow into the cavity 104. In some exemplary embodiments, the cavity 104 is adapted to receive and retain blood flow. In some exemplary embodiments, the cavity 104 is adapted to facilitate the coagulation of the retained blood.

The present invention further discloses a device that is a tooth pod 100 for regenerating a tooth of a patient, comprising: a permeable membrane 103 defined by an inner layer 101 and an outer layer 102, wherein the permeable membrane 103 is adapted to facilitate blood flow via saturation an not microscopic holes; and a cavity 104 defined within the inner layer 101, wherein the cavity 104 is adapted to receive and retain blood flow.

The present invention further discloses a device that is a tooth pod 100 for regenerating a tooth of a patient, comprising: a permeable membrane 103 defined by an inner layer 101 and an outer layer 102, wherein the permeable membrane 103 is adapted to facilitate blood flow; and a cavity 104 defined within the inner layer 101, wherein the cavity 104 is adapted to receive and retain blood flow.

In some exemplary embodiments, the permeable membrane 103 comprises of vitamin E oil and penicillin. In some exemplary embodiments, the permeable membrane 103 is comprised of at least 500 mg of penicillin that is time released. In some exemplary embodiments, the permeable membrane 103 comprises an effective amount of vitamin E oil and penicillin. The term "effective amount" is to be understood as meaning an amount of an active ingredient needed to achieve a desired therapeutic or cosmetic effect.

For example, in a pharmaceutical composition of the invention an effective amount the composition comprising vitamin E oil and penicillin is an amount that is sufficient to promote regeneration of new teeth.

In some exemplary embodiments, the tooth pod 100 is round. FIG. 2 illustrates exemplary dimensions of the inner layer 101 and the outer layer 102 of a tooth pod 100. In some exemplary embodiments, the outer layer 102 of the tooth pod 100 has a diameter approximately ⅛" (1.750 mm). In some exemplary embodiments, the inner layer 101 of the tooth pod 100 has a diameter approximately ¹⁄₁₆" (1.588 mm). In some exemplary embodiments, the tooth pod is round, is exactly the size and shape of a 0.177 mm copper BB, has a ¹⁄₁₆" hollow space in the middle which fills up with blood and then creates, or turns into/grows, a new real tooth.

The tooth pod 100 is implanted into the gum line at approximately ½ the depth of the tooth, which provides space to growth of tooth upwards and downwards. The insertion points of the tooth pod 100 is approximately ranges from ½" to ¾" below the gum line. The blood fills the cavity 104 of the tooth pod 100 and forms new nerve roots. Thereafter, a tooth is formed. They encode by way of DNA from the location they are implanted into the gum line and make the proper tooth for that specific place.

Figure 3:
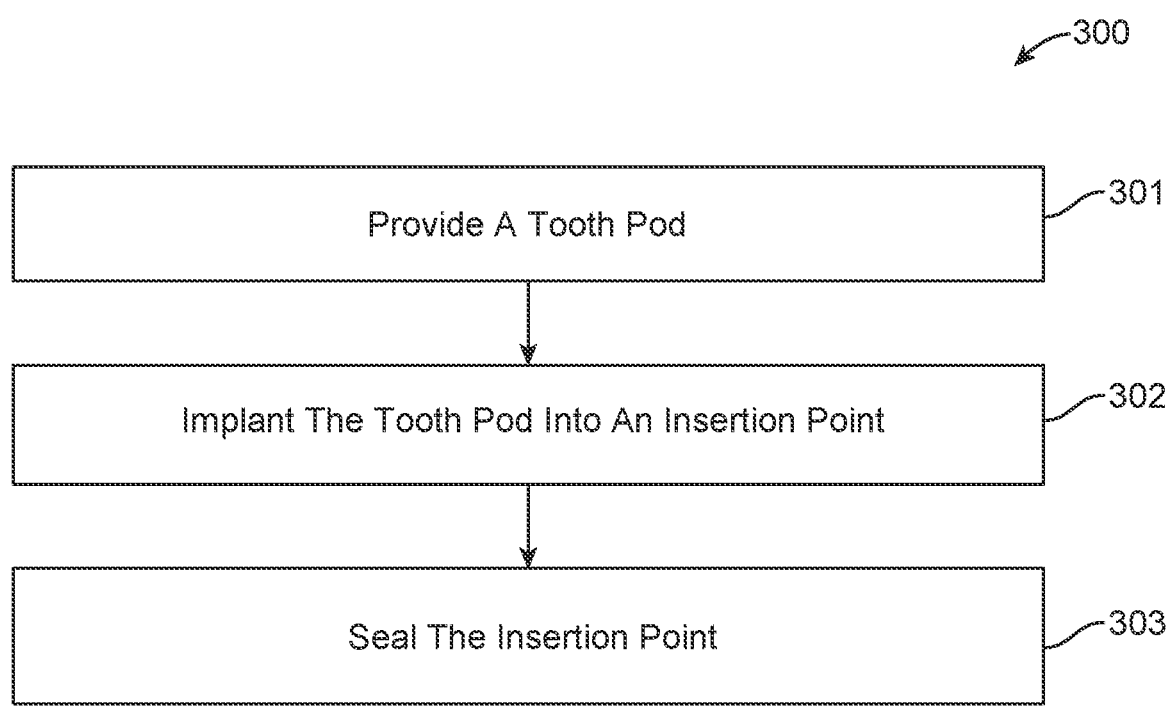
FIG. 3 illustrates a flowchart of a method of implanting a tooth pod in accordance with some exemplary embodiments of the present invention.

Turning to the next figure, FIG. 3 illustrates a flowchart of a method 300 for implanting the tooth pod in accordance with some exemplary embodiments of the present invention. At step 301, the tooth pod 100 is provided. In some exemplary embodiments, the tooth pod comprises of vitamin E oil and penicillin. At step 302, one or more tooth pods 100 are implanted at one or more implant sites where regeneration of teeth are required. In some exemplary embodiments, the tooth pod is implanted at an insertion point situated below a gumline and within a tooth socket of a patient. At step 303, the insertion point is sealed.

In some exemplary embodiments, the permeable membrane 103 is adapted to facilitate blood flow into the cavity, wherein the cavity 104 is adapted to receive and retain blood flow. For example, the cavity is filled with blood which transfers across the permeable membrane 103 made out of penicillin and vitamin E oil. The cavity 104 retains and coagulates the blood flow that enters. In some exemplary embodiments, the coagulation of the blood flow inside the cavity 104 of the tooth pod 100 triggers the body to create nerve roots which next forms a tooth around it.

It is proposed and hypothesized that, within a short period of time, approximately the same amount of time it takes to form a tooth naturally, a real tooth grows into the space previously occupied by the tooth pod 100. The regeneration of a new tooth is prompted by implanting the tooth pod 100 into the patient's jaw line. When blood flows into the cavity 104 of the tooth pod 100 and the blood coagulates, the body of the patient encodes via DNA the formation of a new tooth. The Vitamin E oil and penicillin in the permeable membrane 103 of the tooth pod 100 reduce risk of infection and promote healthy tooth formation.

Advantageously, the present invention discloses a tooth pod 100 and a method 300 that replaces existing dental implant devices by providing a permanent solution by regenerating the teeth.

A method and a device for the regeneration of teeth have been described. The foregoing description of the various exemplary embodiments of the invention has been presented for the purposes of illustration and disclosure. It is not intended to be exhaustive or to limit the invention to the precise form disclosed. Many modifications and variations are possible in light of the above teaching without departing from the spirit of the invention.

What is claimed is:

1. A tooth pod comprising:
   a permeable membrane defined by an inner layer and an outer layer, wherein the permeable membrane is adapted to facilitate blood flow; and
   a cavity defined within the inner layer, wherein the cavity is adapted to receive and retain blood flow.

2. The device of claim 1, wherein the outer layer is adapted to facilitate blood flow.

3. The device of claim 1, wherein the permeable membrane is comprised of vitamin E oil and penicillin.

4. The device of claim 3, wherein the permeable membrane comprising of at least 500 mg of penicillin.

5. The device of claim 3, wherein the permeable membrane is adapted to dissolve.

6. The device of claim 3, wherein the cavity is adapted to receive and retain blood flow through the permeable membrane.

7. The device of claim 3, wherein the device is a round pod.

8. The device of claim 7, wherein the outer layer of the round pod has a diameter approximately 0.177 mm.

9. The device of claim 7, wherein the outer layer of the round pod has a diameter approximately $\frac{1}{8}^{th}$ of an inch (3.175 mm).

10. The device of claim 7, wherein the inner layer of the round pod has a diameter of approximately $\frac{1}{16}^{th}$ of an inch (1.588 mm).

* * * * *